US012746032B2

(12) United States Patent
Nishio

(10) Patent No.: US 12,746,032 B2
(45) Date of Patent: Sep. 29, 2026

(54) MEDICAL DEVICE

(71) Applicant: TERUMO KABUSHIKI KAISHA, Tokyo (JP)

(72) Inventor: Kosuke Nishio, Irvine, CA (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 188 days.

(21) Appl. No.: 18/471,647

(22) Filed: Sep. 21, 2023

(65) Prior Publication Data

US 2024/0016513 A1 Jan. 18, 2024

Related U.S. Application Data

(63) Continuation of application No. PCT/JP2021/011721, filed on Mar. 22, 2021.

(51) Int. Cl.
*A61B 17/3207* (2006.01)

(52) U.S. Cl.
CPC ............................ *A61B 17/320758* (2013.01)

(58) Field of Classification Search
CPC ... A61B 17/22; A61B 17/32; A61B 17/00234; A61B 17/320758; A61B 17/320725; A61B 17/32075; A61B 17/320783
See application file for complete search history.

(56) References Cited

U.S. PATENT DOCUMENTS 5,314,438 A * 5/1994 Shturman ............. A61M 25/01 606/159
6,565,588 B1 5/2003 Clement et al.
(Continued)

FOREIGN PATENT DOCUMENTS

JP 2010509994 A 4/2010
JP 2011517601 A 6/2011
(Continued)

OTHER PUBLICATIONS

International Search Report (PCT/ISA/210) with English translation and Written Opinion (PCT/ISA/237) mailed on May 25, 2021, by the Japan Patent Office as the International Searching Authority for International Application No. PCT/JP2021/011721.
(Continued)

*Primary Examiner* — Tuan V Nguyen
(74) *Attorney, Agent, or Firm* — BUCHANAN INGERSOLL & ROONEY PC

(57) ABSTRACT

A medical device insertable into a living body lumen includes a drive shaft that rotates in a predetermined direction of rotation in response to a proximal side driving force to transmit a rotational force in a distal direction. The drive shaft includes: an inner coil of plural wires wound side-by-side in a circumferential direction of the drive shaft; and an outer coil of plural wires wound side-by-side in the circumferential direction of the drive shaft and surrounding the inner coil. The inner coil wires are wound in the predetermined direction of rotation in the distal direction as viewed from the proximal side, and the outer coil wires are wound in a direction opposite the predetermined direction of rotation in the distal direction as viewed from the proximal side. The number of wires constituting the inner coil is smaller than the number of wires constituting the outer coil.

21 Claims, 6 Drawing Sheets

(56) References Cited

U.S. PATENT DOCUMENTS

| | | | | |
|---|---|---|---|---|
| 2002/0007190 | A1* | 1/2002 | Wulfman ....... | A61B 17/320725 606/171 |
| 2003/0139689 | A1 | 7/2003 | Shturman et al. | |
| 2008/0228171 | A1 | 9/2008 | Kugler et al. | |
| 2009/0234378 | A1 | 9/2009 | Escudero et al. | |
| 2010/0063534 | A1 | 3/2010 | Kugler et al. | |
| 2015/0150587 | A1* | 6/2015 | Smith ............ | A61B 17/320758 606/159 |
| 2016/0256620 | A1 | 9/2016 | Scheckel et al. | |
| 2018/0317954 | A1* | 11/2018 | Jamous ............ | A61B 17/32002 |
| 2019/0060608 | A1 | 2/2019 | Bridgeman et al. | |
| 2020/0078038 | A1 | 3/2020 | Fleming et al. | |
| 2021/0275210 | A1 | 9/2021 | Nishio et al. | |

FOREIGN PATENT DOCUMENTS

| | | | | |
|---|---|---|---|---|
| JP | 2016538982 | A | 12/2016 | |
| JP | 2019146968 | A | 9/2019 | |
| WO | WO-2020026216 | A1 * | 2/2020 | ..... A61B 17/320758 |
| WO | 2020105210 | A1 | 5/2020 | |

OTHER PUBLICATIONS

English Translations of the International Search Report (Form PCT/ISA/210) and the Written Opinion of the International Searching Authority (Form PCT/ISA/237) issued May 25, 2021, by the Japan Patent Office in corresponding International Application No. PCT/JP2021/011721. (7 pages).

* cited by examiner

MEDICAL DEVICE

CROSS-REFERENCES TO RELATED APPLICATIONS

This application is a continuation of International Application No. PCT/JP2021/011721 filed on Mar. 22, 2021, the entire content of which is incorporated herein by reference.

TECHNOLOGICAL FIELD

The present invention generally relates to a medical device to be inserted into a living body lumen.

BACKGROUND DISCUSSION

Examples of a method for treating a stenosed part due to plaque, thrombus, or the like in a blood vessel include a method for expanding the blood vessel with a balloon and a method for placing a meshed or coiled stent in the blood vessel as a support of the blood vessel. However, with these methods, it is difficult to treat a stenosed part caused by a plaque or the like hardened due to calcification or a stenosed part generated in a bifurcation of a blood vessel. An atherectomy device (see, for example, U.S. Pat. No. 6,565,588) is an example of a device that can provide treatment even in such a case.

The atherectomy device removes plaque in a blood vessel by shearing/breaking up the plaque by a cutting portion rotating at high speed. The atherectomy device includes a drive shaft disposed within a catheter. The drive shaft transmits high-speed rotation of a cutting component disposed at the distal end of the catheter from outside the body.

SUMMARY

The drive shaft needs to have stable high-speed rotation and sufficient durability against a torque load during cutting of a lesion such as a plaque. There are a plurality of cases where the drive shaft is formed using a single-layer coil. However, when the drive shaft formed using a single-layer coil receives a strong torque load, plastic deformation occurs in the coil, and there is a possibility that a hollow structure cannot be properly maintained.

The medical device disclosed here can properly maintain the structure of a drive shaft even when receiving a strong torque.

A medical device disclosed here is elongated and insertable into a living body lumen, the medical device including a drive shaft having a distal end and a proximal end and having a predetermined direction of rotation, the drive shaft being rotatable in response to a driving force from a proximal side to transmit a rotational force in a distal direction. The drive shaft includes: an inner coil formed by winding a plurality of wires side-by-side in a circumferential direction of the drive shaft; and an outer coil formed by winding a plurality of wires side-by-side in the circumferential direction of the drive shaft and surrounding the inner coil, the wires of the inner coil are wound in the direction of rotation in the distal direction as viewed from the proximal side, the wires of the outer coil are wound in a direction opposite to the predetermined direction of rotation in the distal direction as viewed from the proximal side, and a number of the wires constituting the inner coil is smaller than a number of the wires constituting the outer coil.

In the medical device configured as described above, the number of the wires constituting the inner coil is smaller than the number of the wires constituting the outer coil, and thus, during rotation of the drive shaft in the predetermined direction of rotation, a balance between power of the outer coil to contract and power of the inner coil to expand is improved, and the torsional rigidity of the drive shaft can be improved. Therefore, the medical device can suppress plastic deformation of the drive shaft due to strong torque, and can properly maintain the structure of the drive shaft.

According to another aspect, a medical device to cut an object in a living body lumen comprises a rotatable elongated drive shaft that is rotatable in a first direction of rotation in response to a driving force applied to the elongated drive shaft and a cutting portion operatively connected to the elongated drive shaft so that rotation of the elongated drive shaft in the first direction of rotation results in rotation of the cutting portion. The cutting portion has an outer surface configured to cut the object in the living body lumen when the cutting portion is rotated while the cutting portion is positioned in the living body lumen. The drive shaft comprises an outer coil and an inner coil, with the outer coil surrounding the inner coil so that the outer coil covers an outer surface of the inner coil. The inner coil is comprised of a total number N1 of wires that extend helically in side-by-side relation to one another, with the total number N1 of wires extending helically in the first direction of rotation in the distal direction as viewed from the proximal side, and the total number N1 being a number greater than one. The outer coil is comprised of a total number N2 of wires that extend helically in side-by-side relation to one another, with the total number N2 of wires extending helically in a direction opposite the first direction of rotation in the distal direction as viewed from the proximal side, and the total number N2 being a number greater than one. The ratio of N1/N2 is less than 1.

In accordance with another aspect, a method comprises: introducing a cutting portion into a living body lumen, with the cutting portion being operatively connected to a rotatable drive shaft so that rotation of the drive shaft in one rotation direction results in rotation of the cutting portion; advancing the cutting portion in the living body lumen to position the cutting portion adjacent a lesion area in the living body lumen; and rotating the drive shaft in the one rotation direction to rotate the cutting portion while the cutting portion is in contact with the lesion area to cut the lesion area. The drive shaft comprises: an outer coil and an inner coil, the outer coil surrounding the inner coil; the inner coil being comprised of a total number N1 of wires that extend helically in side-by-side relation to one another, the total number N1 of wires extending helically in the first direction of rotation in the distal direction as viewed from the proximal side, the total number N1 being a number greater than one; the outer coil being comprised of a total number N2 of wires that extend helically in side-by-side relation to one another, the total number N2 of wires extending helically in a direction opposite the first direction of rotation in the distal direction as viewed from the proximal side, the total number N2 being a number greater than one; and the ratio of N1/N2 is less than 1.

BRIEF DESCRIPTION OF THE DRAWINGS

FIGS. 7A-7C are schematic diagrams illustrating a state of removing a lesion by the medical device, in which FIG. 7A illustrates a state in which cutting is started, FIG. 7B illustrates a state in which cutting is performed by rotating an outer tube shaft, and FIG. 7C illustrates a state in which cutting is performed while moving the outer tube shaft.

DETAILED DESCRIPTION

Figure 1:
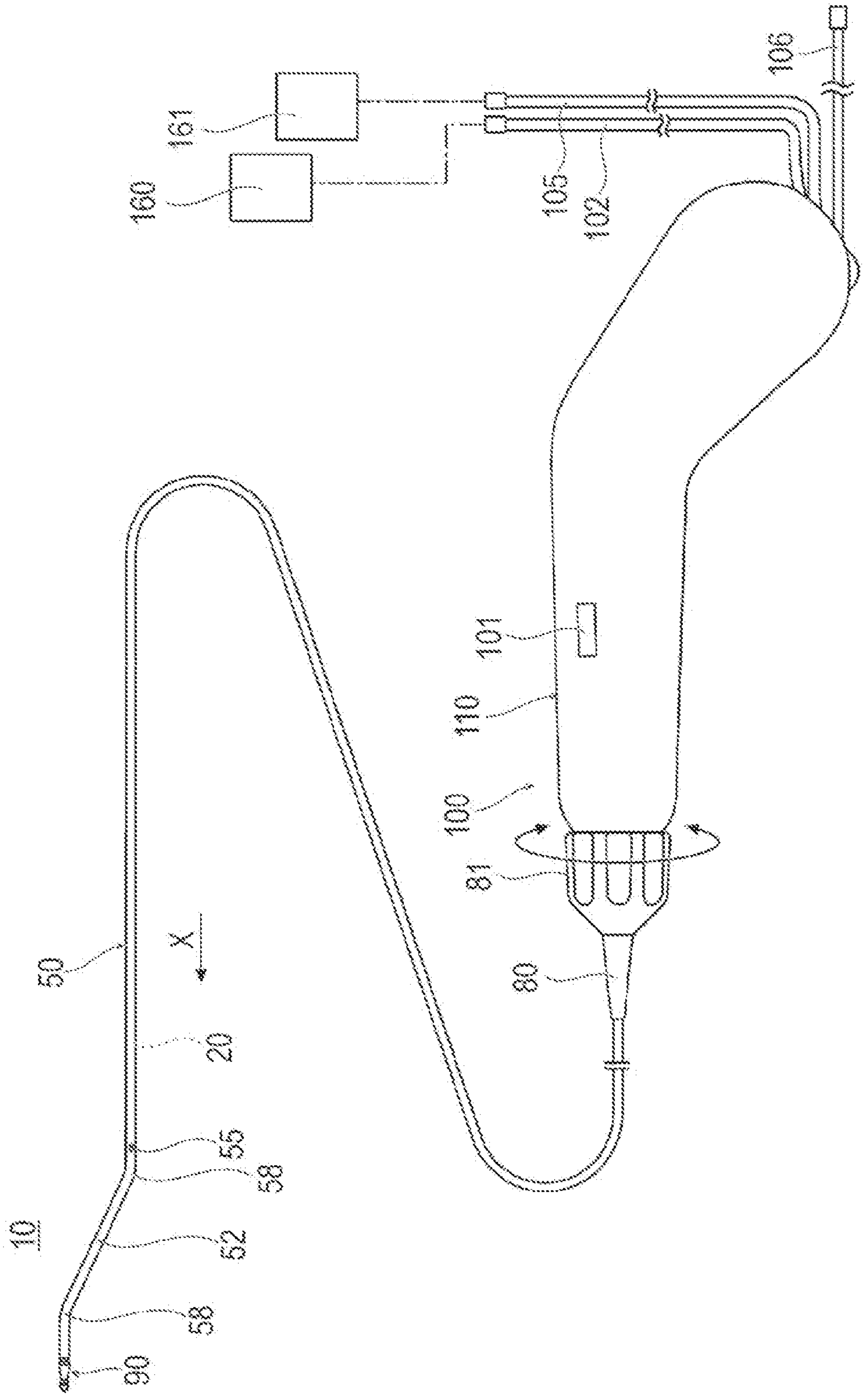
FIG. 1 is a plan view illustrating a medical device according to an embodiment.

Set forth below with reference to the accompanying drawings is a detailed description of embodiments of a medical device representing an example of the new medical device disclosed here. The size and ratio of each member in the drawings may be exaggerated for convenience of description and may be different from the actual size and ratio. Herein, a side of the medical device to be inserted into a living body lumen is referred to as "distal side" and a side to be operated is referred to as "proximal side."

A medical device 10 according to the present embodiment is inserted into a blood vessel in acute or chronic lower limb ischemia or deep-vein thrombosis, and used for a treatment including breaking up and removing an object such as a thrombus, a plaque, an atheroma, and a calcified lesion. The object to be removed is not necessarily limited to a thrombus, a plaque, an atheroma, and a calcified lesion, and may be any object that can be present in the living body lumen.

As illustrated in FIG. 1, the medical device 10 includes a long or elongated drive shaft 20 to be rotationally driven, an outer tube shaft (tubular shaft) 50 accommodating the drive shaft 20, a cutting portion 90 for cutting thrombus or the like, a guide wire lumen tube 40 (shown in FIG. 3) disposed inside the drive shaft 20, and a handle 100. The medical device 10 further includes a distal bearing 53 (shown in FIG. 3) disposed on the distal side of the outer tube shaft 50, and a rotation shaft 24 disposed between the drive shaft 20 and the cutting portion 90.

Figure 3:
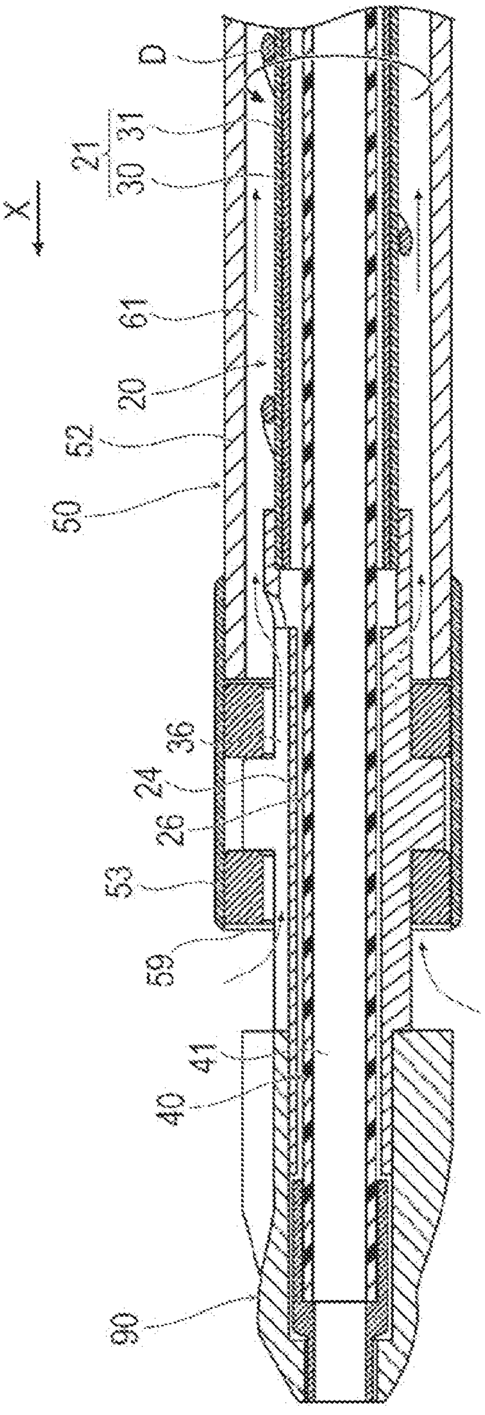
FIG. 3 is a cross-sectional view illustrating a distal end part of the medical device.
Figure 4:
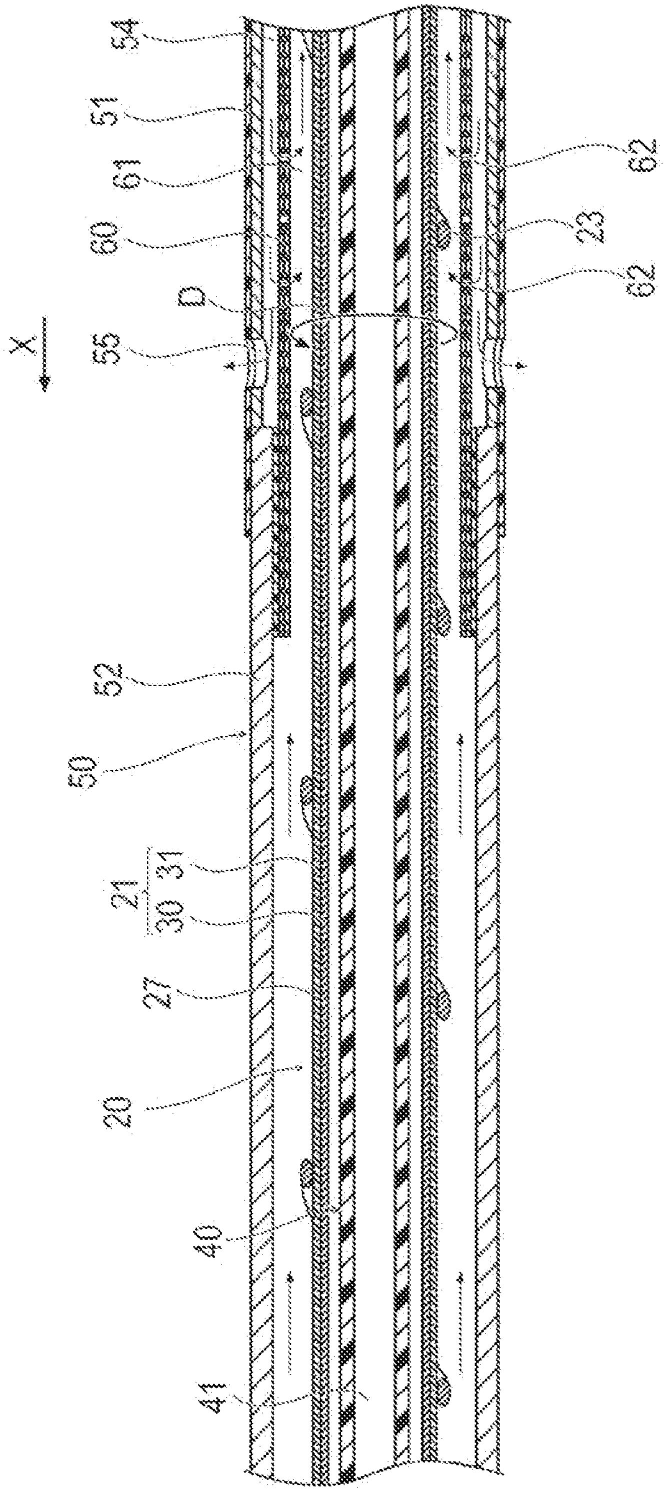
FIG. 4 is a cross-sectional view illustrating a section of the medical device that is proximal to the distal end part.
Figure 5:
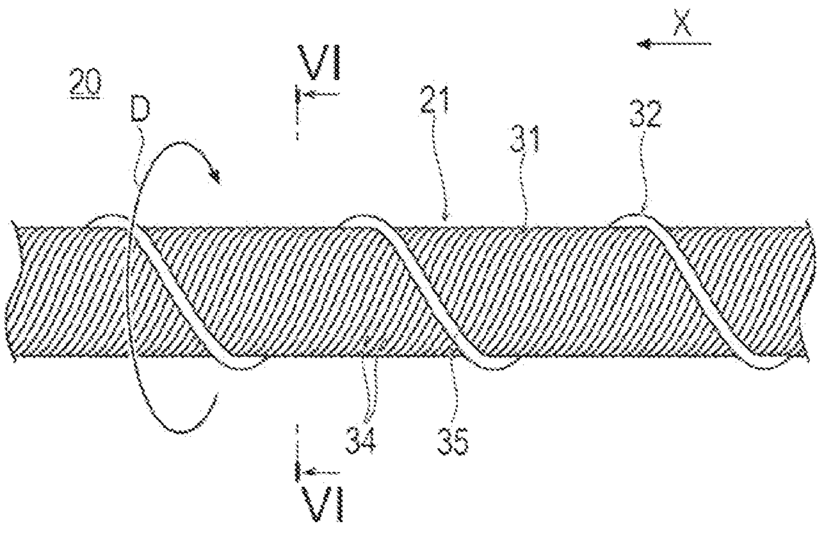
FIG. 5 is a plan view of a drive shaft.

As illustrated in FIGS. 1, 3, and 4, the outer tube shaft 50 is a long or elongated tubular body that accommodates the drive shaft 20. The outer tube shaft 50 rotates together with an operation portion 81 fixed to the proximal end part of the outer tube shaft 50 when an operator rotates the operation portion 81 with his/her finger. The cutting portion 90 can be directed to the lesion by rotating the outer tube shaft 50. The outer tube shaft 50 includes an outer layer 51, an inner layer 60, and a shaping distal end portion 52.

Figure 2:
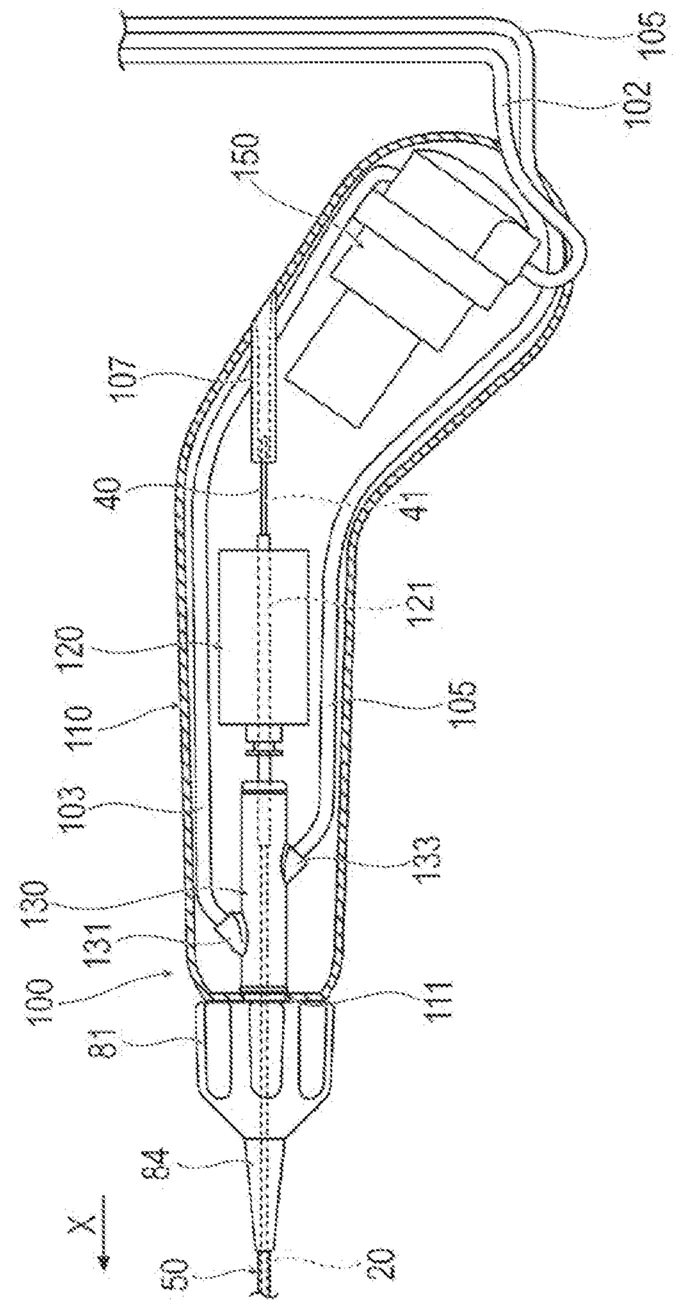
FIG. 2 is a diagram illustrating a casing of a handle of the medical device in cross section and illustrating the other sections in plan view.

At least one side hole 55 penetrating from the inner peripheral surface to the outer peripheral surface is formed at the distal end part of the outer layer 51. As illustrated in FIGS. 1 and 2, the operation portion 81 and a kink protector 84 are fixed to the outer peripheral surface of the outer layer 51 at the proximal end part of the outer layer 51. The kink protector 84 suppresses kinking at the proximal end part of the outer tube shaft 50. The distal end part of the outer layer 51 is fixed to the proximal end part of the shaping distal end portion 52. It is preferable that the outer layer 51 has flexibility so as to bend in the living body lumen and has high torque transmission. Examples of the material that can be used for the outer layer 51 include a material obtained by forming a helical slit or groove by laser processing in a circular tube made of a metal material or a resin material having a certain degree of strength.

The inner layer 60 is disposed on the inner side of the outer layer 51 with a gap therebetween as illustrated in FIG. 4. A first lumen 54 for delivering a liquid such as physiological saline in a distal direction X is formed between the outer layer 51 and the inner layer 60. At least one through hole 62 penetrating from the outer peripheral surface to the inner peripheral surface is formed in the inner layer 60. The distal end part of the inner layer 60 is fixed to the inner peripheral surface of the shaping distal end portion 52. The proximal end part of the inner layer 60 protrudes further to the proximal side with respect to the outer layer 51. That is, the proximal end part of the inner layer 60 protrudes proximally beyond the proximal end of the outer layer 51. A second lumen 61 for discharging an object such as a cut thrombus in the proximal direction is formed inside the inner layer 60 and the shaping distal end portion 52 on the distal side of the inner layer 60.

The inner layer 60 preferably has a structure capable of flexibly bending and capable of maintaining a cross-sectional shape even when bent in order to properly maintain a gap with the rotatable drive shaft 20 accommodated therein. To this end, the inner layer 60 is formed by embedding a braided wire obtained by braiding a metal wire in a tubular shape or a coil wire in a resin material.

As illustrated in FIGS. 1, 3, and 4, the shaping distal end portion 52 is located at the distal end part of the outer tube shaft 50. The shaping distal end portion 52 is bent at two bending portions 58 such that the axis of the shaping distal end portion 52 at the proximal end part and the axis at the distal end part are shifted from each other. The number of the bending portions 58 may be one or three or more. By rotating the outer tube shaft 50, the shaping distal end portion 52 can direct the cutting portion 90 toward the lesion and further strongly press the cutting portion 90 against the lesion. As the material from which the shaping distal end portion 52 may be fabricated, a material like the materials described above for the outer layer 51 may be used, for example. In particular, it is preferable to use a NiTi alloy having superelasticity as the material of the shaping distal end portion 52.

As illustrated in FIG. 3, the distal bearing 53 is connected to the distal end part of the outer tube shaft 50 and rotatably supports the rotation shaft 24 connected to the distal end part of the drive shaft 20. The distal bearing 53 is fixed to the distal end part of the shaping distal end portion 52. The distal bearing 53 has, at the distal end, a distal end opening 59 for taking an object such as a cut thrombus, blood, and liquid discharged through the side hole 55 into the second lumen 61. The distal end of the distal bearing 53 is positioned proximal to the cutting portion 90.

The cutting portion 90 is a member for cutting and shrinking (reducing the size of) an object such as thrombus, plaque, and calcified lesion. Therefore, the term "cut" means applying a force to an object in contact with the cutting portion 90 and shrinking or reducing the size of the object. A method for applying a force during cutting, and the shape or type of the cut object after cutting are not limited. The cutting portion 90 is strong enough to cut the above-mentioned object. The cutting portion 90 is fixed to the outer peripheral surface of the drive shaft 20 at the distal end part of the drive shaft 20. The cutting portion 90 has a large number of fine abrasive grains on the surface. Alternatively, the cutting portion 90 may have a sharp blade.

It is preferable that the material of the cutting portion 90 is strong enough to cut thrombus, and examples of the material that can be preferably used include stainless steel, Ta, Ti, Pt, Au, W, a NiTi alloy, a shape memory alloy, a supersteel alloy, and ceramics.

The drive shaft 20 is a flexible tubular body which has a distal end and a proximal end, and which transmits a rotational force input from the proximal side to the cutting portion 90 via the rotation shaft 24 disposed on the distal side of the drive shaft 20 as illustrated in FIGS. 1 to 6. The drive shaft 20 has a predetermined (predefined) direction of rotation D (a rotation direction of the drive shaft 20 when the medical device 10 is used for cutting and conveyance). The distal end part of the drive shaft 20 is connected to the cutting portion 90, and the proximal end part of the drive shaft 20 is connected to a power shaft 121 of the drive unit 120 provided on the handle 100. The drive shaft 20 is rotatable inside the outer tube shaft 50. The drive shaft 20 includes a multilayer coil 21.

The multilayer coil 21 is formed by stacking a plurality of coils in layers. The multilayer coil 21 includes an inner coil 30, an outer coil 31 surrounding the outside of the inner coil 30, and a conveyance coil 32 surrounding the outside of the outer coil 31. The multilayer coil 21 may include coils of four or more layers.

The inner coil 30 is formed by intertwining a plurality of first wires 33. The plurality of first wires 33 is spirally wound side-by-side in close contact with each other to form one layer. The plurality of first wires 33 is wound in a direction in which the spiral of the first wires 33 is loosened and increased in diameter when the drive shaft 20 receives a load torque from the distal side during rotation in the predetermined direction of rotation D due to a torque from the proximal side. That is, the first wires 33 are wound in the predetermined direction of rotation D in the distal direction X when viewed from the proximal side. The inner coil 30 has a characteristic of contracting along the center of the axis of the coil while increasing in diameter when the drive shaft 20 receives a load torque during rotation in the predetermined direction of rotation D.

The outer coil 31 is formed by intertwining a plurality of second wires 34. The plurality of second wires 34 is spirally wound side-by-side in close contact with each other to form one layer. The plurality of second wires 34 is wound in a direction in which the spiral of the second wires 34 is tightened and decreased in diameter when the drive shaft 20 receives a load torque from the distal side during rotation in the predetermined direction of rotation D due to a torque from the proximal side. That is, the second wires 34 are wound in the direction opposite to the predetermined direction of rotation D in the distal direction X when viewed from the proximal side. The outer coil 31 has a characteristic of extending along the center of the axis of the coil while decreasing in diameter when the drive shaft 20 receives a load torque during rotation in the predetermined direction of rotation D.

The outer coil 31 is disposed in close contact with the outer peripheral surface of the inner coil 30. Therefore, when the drive shaft 20 receives a load torque during rotation in the predetermined direction of rotation D, the inner coil 30 is going to contract in the axial direction while increasing in diameter, and the outer coil 31 is going to extend in the axial direction while reducing in diameter, so that the displacements of the inner coil 30 and the outer coil 31 in the radial direction and the axial direction are canceled out. Thus, the multilayer coil 21 including the inner coil 30 and the outer coil 31 can reduce deformation in the radial direction and the axial direction when the drive shaft 20 rotates in the predetermined direction of rotation D.

Figure 6:
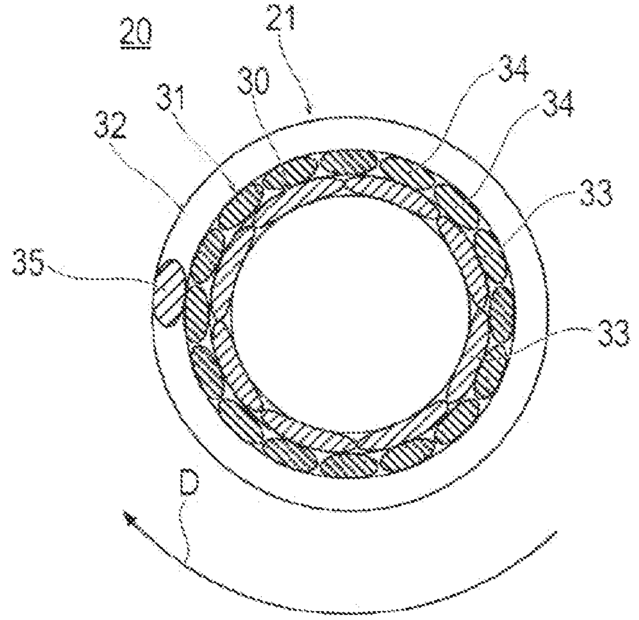
FIG. 6 is a cross-sectional view taken along the section line VI-VI in FIG. 5.

The number (i.e., total number) N1 of the first wires 33 of the inner coil 30 is smaller than the number (i.e., total number) N2 of the second wires 34 of the outer coil 31. The number N2 of the second wires 34 is at least 2, preferably 6 to 18, more preferably 8 to 18, and still more preferably 10 to 16. The combination of the number N1 of the first wires 33 and the number N2 of the second wires 34 is not particularly limited, but for example, when the number N2 is 16, the number N1 is 4, 6, 8, 10, 12, or 14. In the present embodiment, the number N2 of the second wires 34 is 16, and the number N1 of the first wires 33 is 8 as illustrated in FIG. 6.

The number N1 of the first wires 33 is not particularly limited as long as it is smaller than the number N2 of the second wires 34. A ratio Ra of the numbers of wires, which is a ratio (N1/N2) of the number N1 of the first wires 33 to the number N2 of the second wires 34, is less than 1, preferably 0.875 or less, more preferably or less, and still more preferably 0.625 or less. Furthermore, the ratio Ra is larger than 0, preferably 0.25 or more, more preferably 0.375 or more, and still more preferably 0.5 or more. When the ratio Ra is close to 1, it is considered that the power of the inner coil 30 to expand is larger than the power of the outer coil 31 to contract, and the outer coil 31 is likely to be plastically deformed. When the ratio Ra is close to 0, it is considered that the power of the inner coil 30 to expand is smaller than the power of the outer coil 31 to contract, and the inner coil 30 is likely to be plastically deformed.

The conveyance coil 32 is disposed in close contact with the outer peripheral surface of the outer coil 31 so as to form the outermost layer of the drive shaft 20. The conveyance coil 32 is formed by loosely winding a third wire 35 constituting the conveyance coil 32 at intervals that that there is an axial spacing between axially adjacent windings of the third wire 35. The number of the third wire 35 is one in the present embodiment, but may be two or more. The conveyance coil 32 functions as an Archimedean screw (screw pump) when the drive shaft 20 rotates in the predetermined direction of rotation D, and conveys a liquid or an object in the proximal direction. To this end, the third wire 35 is wound in the predetermined direction of rotation D in the distal direction X when viewed from the proximal side. The conveyance coil 32 may be wound in a direction opposite to the predetermined direction of rotation D in the distal direction X when viewed from the proximal side. As a result, the conveyance coil 32 functions as an Archimedean screw (screw pump) when the drive shaft 20 rotates in the predetermined direction of rotation D, and can convey liquid or an object in the distal direction. Alternatively, the conveyance coil 32 may be disposed in close contact with the inner peripheral surface of the inner coil 30 so as to form the innermost layer of the drive shaft 20. In this case, the conveyance coil 32 can also convey the liquid or the object inside the drive shaft 20 in the distal direction or the proximal direction depending on the winding direction. In addition, the conveyance coil 32 may not be provided in the medical device 10.

Examples of the material that can be preferably used for the first wires 33, the second wires 34, and the third wire 35 include stainless steel, Ta, Ti, Pt, Au, W, polyolefin such as polyethylene and polypropylene, polyamide, polyester such as polyethylene terephthalate, fluorine-based polymer such as ethylene-tetrafluoroethylene copolymer (ETFE), polyetheretherketone (PEEK), and polyimide. Each of the first wire 33, the second wire 34, and the third wire 35 is formed of one single wire, but may be, for example, a wire such as a stranded wire made up of a collection of a plurality of single wires formed into a bundle.

The rotation shaft 24 is rotatably supported by the distal bearing 53 connected to the distal end part of the outer tube shaft 50. The proximal end part of the rotation shaft 24 is fixed to the multilayer coil 21, and the distal end part of the rotation shaft 24 is fixed to the cutting portion 90. The rotation shaft 24 is formed with at least one groove-shaped passage 36 extending along the center of the axis. The passage 36 allows an object cut by the cutting portion 90 to pass in the proximal direction through the inside of the distal bearing 53.

The guide wire lumen tube 40 is a tubular body disposed inside the drive shaft 20 as illustrated in FIGS. 3 and 4. The guide wire lumen tube 40 is formed with a guide wire lumen 41 through which a guide wire passes. The guide wire lumen tube 40 prevents the guide wire passing through the guide wire lumen 41 from rubbing against the drive shaft 20. The distal end part of the guide wire lumen tube 40 protrudes further to the distal side with respect to the drive shaft 20 (the distal end part of the guide wire lumen tube 40 protrudes distally beyond the distal end of the drive shaft 20) and is disposed inside the cutting portion 90. A proximal end part of the guide wire lumen tube 40 is connected to a proximal end tube 107 through which the guide wire is introduced, the proximal end tube 107 being disposed on the handle 100, as illustrated in FIG. 2.

The handle 100 is a section operated by the operator as illustrated in FIGS. 1 and 2. The handle 100 includes a casing 110, the drive unit 120, a housing 130, and a liquid feeder 150. The handle 100 further includes a switch 101, a suction tube 102, a liquid feeding tube 103, a discharge tube 105, an electric cable 106, and the proximal end tube 107.

The casing 110 constitutes an outer shell of the handle 100. The casing 110 houses the drive unit 120, the housing 130, the liquid feeding tube 103, a part of the discharge tube 105, and a part of the electric cable 106. A passage hole 111 through which the drive shaft 20, the outer tube shaft 50, and the guide wire lumen tube 40 pass is formed at a distal end part of the casing 110. The proximal end part of the guide wire lumen tube 40 is connected to the proximal end tube 107. The proximal end tube 107 has a lumen communicating with the guide wire lumen 41, and guides the guide wire to the proximal side.

The drive unit 120 is, for example, a hollow motor. The drive unit 120 includes a hollow power shaft 121 that rotates by power supplied from the outside via the electric cable 106. The power shaft 121 houses the drive shaft 20 therein and is fixed to the drive shaft 20. The rotational speed of the power shaft 121 is not particularly limited, and is, for example, 5,000 to 200,000 rpm. The drive unit 120 is connected to a control device (not illustrated), and can be controlled from the inside or the outside of the handle 100.

The electric cable 106 can be connected to an external power supply or control device. The switch 101 is a section operated by the operator to activate or stop the drive unit 120. The switch 101 is located on the outer surface of the casing 110. When a battery is provided in the handle 100, the electric cable 106 is located in the handle 100 and connected to the battery. In a case where the electric cable 106 is connected to an external power supply, it is possible to perform signal processing on an operation input of the switch 101 and control the drive unit 120 and the liquid feeder 150 by providing the control device (not illustrated) in the handle 100.

The operation portion 81 is a section operated by the operator with his/her finger to apply rotational torque to the outer tube shaft 50. The outer tube shaft 50 is fixed to the inside of the operation portion 81.

The housing 130 includes a liquid feed port 131 through which liquid is fed and a discharge port 133 through which liquid or an object is discharged. The liquid feed port 131 communicates with the first lumen 54 formed between the outer layer 51 and the inner layer 60 of the outer tube shaft 50. The liquid feed port 131 is connected to the liquid feeding tube 103 and can receive liquid from the liquid feeding tube 103. The liquid fed to the liquid feed port 131 can flow into the first lumen 54 of the outer tube shaft 50. The discharge port 133 communicates with the second lumen 61 formed between the outer tube shaft 50 and the drive shaft 20. The discharge port 133 is connected to the discharge tube 105. The discharge port 133 can receive a liquid or an object from the second lumen 61 and discharge the liquid or the object to the discharge tube 105.

The liquid feeder 150 is a pump that feeds liquid to the housing 130 via the liquid feeding tube 103. The liquid feeder 150 is connected to the suction tube 102 that receives supply of a liquid such as physiological saline from a liquid feeding source outside the casing 110, and can suck the liquid from the suction tube 102. The liquid feeder 150 is connected to the liquid feeding tube 103 and can discharge the sucked liquid to the liquid feeding tube 103. The external liquid feeding source is, for example, a physiological saline bag 160, but is not limited thereto. The liquid feeder 150 may be provided outside instead of being provided in the handle 100. The liquid feeder 150 is not limited to a pump as long as a liquid feeding pressure can be generated, and may be, for example, a syringe, a bag suspended from an IV stand, or a pressurized bag. Furthermore, the liquid feeder 150 may use, for example, the conveying force by the conveyance coil 32 of the drive shaft 20 without having a pump. In this case, the conveyance coil 32 is wound in a direction in which the conveyance coil 32 applies a force toward the distal side to the liquid by the rotation of the drive shaft 20 in the predetermined direction of rotation. Then, for example, the physiological saline bag 160 functioning as a liquid feeder is connected to the discharge port 133 functioning as a liquid feed port. As a result, the rotating conveyance coil 32 can convey the physiological saline supplied from the physiological saline bag 160 to the second lumen 61 through the discharge port 133 in the distal direction.

The discharge tube 105 is a tube for discharging liquid or an object to the outside of the casing 110. The discharge tube 105 is connected to, for example, a waste liquid bag 161 that can store a liquid or an object. The discharge tube 105 may be connected to a suction source that can actively suck, such as a pump or a syringe.

Next, a method of using the medical device 10 according to the embodiment will be described. Here, a case where a calcified lesion L in the blood vessel is broken up and conveyed will be described as an example.

Figure 7A:
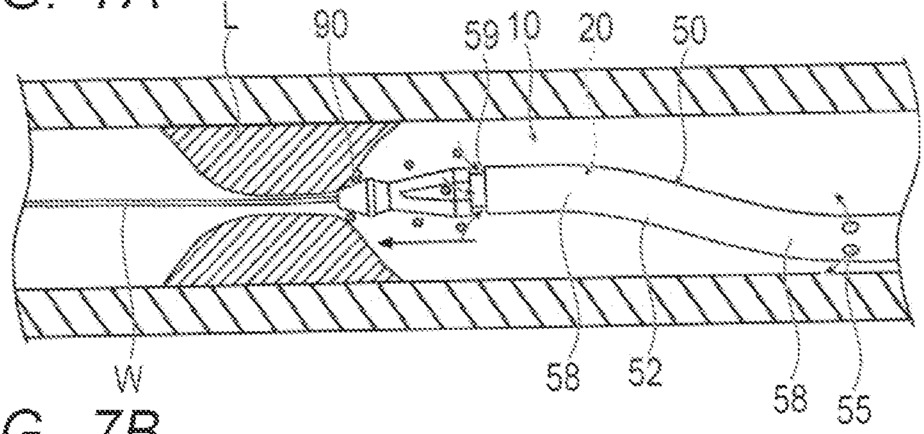

First, the operator inserts the guide wire W into the blood vessel and brings or moves the guide wire W to the vicinity of the lesion L. Next, the operator inserts the proximal end of the guide wire W into the guide wire lumen 41 of the medical device 10. Thereafter, the operator moves the cutting portion 90 of the medical device 10 to the vicinity of the lesion L using the guide wire W as a guide as illustrated in FIG. 7(A).

Next, the operator operates the switch 101 to start the operations of the drive unit 120 and the liquid feeder 150. Thus, the power shaft 121 of the drive unit 120 rotates, and the drive shaft 20 fixed to the power shaft 121 and the cutting portion 90 connected to the drive shaft 20 via the rotation shaft 24 rotate. Accordingly, the operator can cut the lesion L by the cutting portion 90. When the power shaft 121 rotates, the conveyance coil 32 disposed on the outer peripheral surface of the drive shaft 20 generates a force for conveying the liquid or the object in the second lumen 61 to the proximal side as illustrated in FIG. 4. Thus, a conveying force acts on the distal end opening 59 of the outer tube shaft 50 as illustrated in FIGS. 3 and 7(A).

Figure 7B:
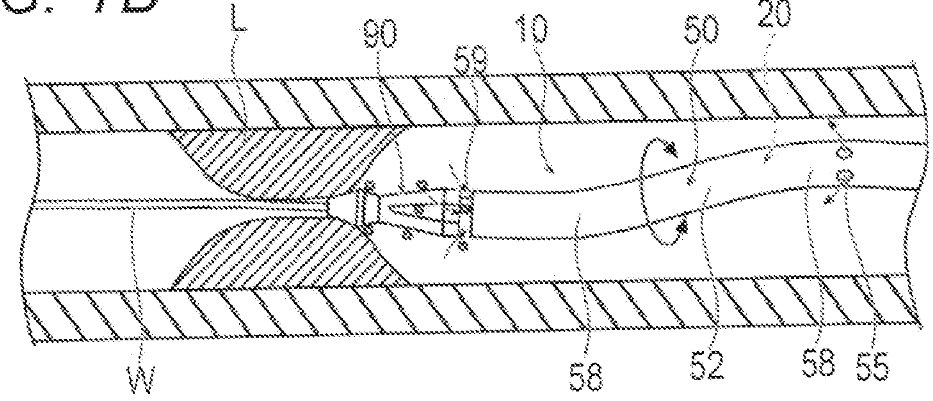
Figure 7C:
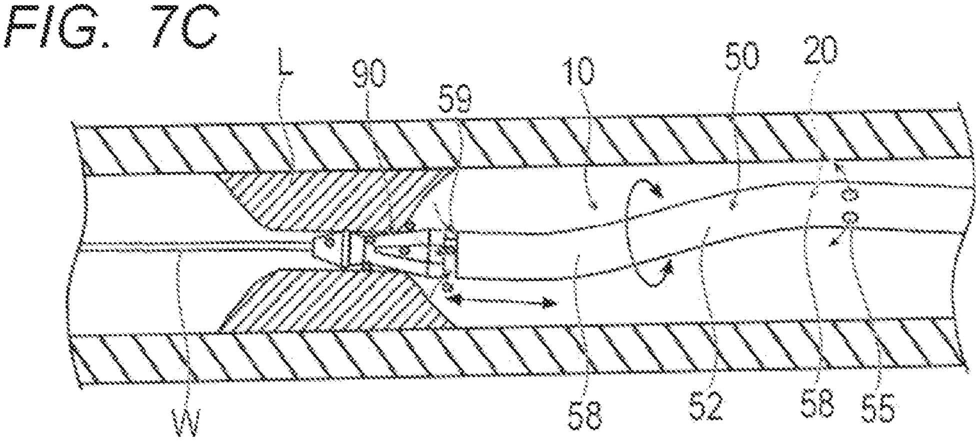

The operator can change the position of the cutting portion 90 in the circumferential direction by operating the operation portion 81 illustrated in FIGS. 1 and 2. When the operator turns the operation portion 81, the outer tube shaft 50 fixed to the operation portion 81 rotates. When the outer tube shaft 50 rotates, the position and direction of the portion of the outer tube shaft 50 distal to the bending portion 58 change, and the position and direction of the cutting portion 90 can be changed, as illustrated in FIG. 7(B). Therefore, cutting can be performed while changing the position and direction of the cutting portion 90 only by operating the operation portion 81 without rotating the entire handle 100 that is difficult to rotate greatly. Further, the operator moves the outer tube shaft 50 back and forth along the longitudinal direction of the blood vessel by moving the entire handle 100 or the outer tube shaft 50 exposed to the outside of the body. As a result, the lesion L can be cut along the longitudinal direction of the blood vessel by the cutting portion 90 as illustrated in FIG. 7(C).

When the operation of the liquid feeder 150 is started, a physiological saline is sucked from the suction tube 102 into the liquid feeder 150 and discharged to the liquid feeding tube 103 as illustrated in FIGS. 1 and 2. The physiological saline discharged to the liquid feeding tube 103 flows from the liquid feed port 131 into the first lumen 54 between the outer layer 51 and the inner layer 60 as illustrated in FIG. 4.

The physiological saline that has entered the first lumen 54 from the liquid feed port 131 moves in the distal direction. The physiological saline flowing through the first lumen 54 in the distal direction is released into the blood vessel through the side hole 55 formed at the distal end part of the outer layer 51 as illustrated in FIGS. 4 and 7. In addition, a part of the physiological saline flowing through the first lumen 54 in the distal direction passes through the through hole 62 and flows into the second lumen 61 which is on the inner side. A portion of the physiological saline released into the blood vessel is conveyed together with blood and the cut object to the second lumen 61 through the distal end opening 59 of the outer tube shaft 50 as illustrated in FIGS. 3 and 7. The object and the liquid that have entered the second lumen 61 move in the second lumen 61 in the proximal direction. The object and blood conveyed to the second lumen 61 are diluted by the physiological saline released into the blood vessel through the side hole 55. Furthermore, the object and the liquid conveyed to the second lumen 61 are diluted by the physiological saline flowing directly into the second lumen 61 through the through hole 62 as illustrated in FIG. 4. Therefore, it is possible to reduce the viscosity of the discharged object and to suppress the formation of thrombus in the second lumen 61. Accordingly, it is possible to improve the conveyance performance while suppressing a decrease in the conveying force or damage of the medical device 10 due to the formation of thrombus in the second lumen 61. In addition, it is possible to suppress the thrombus formed in the medical device 10 from flowing out into the living body lumen. Mixing an anticoagulant such as heparin into physiological saline in advance is effective to enhance the effect of suppressing formation of thrombus.

When moving in the proximal direction through the second lumen 61, the liquid and the object that have entered the second lumen 61 are discharged from the discharge port 133 to the external waste liquid bag 161 through the discharge tube 105 as illustrated in FIG. 1.

Excessive load torque may act on the drive shaft 20 rotating in the predetermined direction of rotation D due to, for example, excessive cutting resistance or contact between the inner peripheral surface of the outer tube shaft 50 and the outer peripheral surface of the drive shaft 20 because of the outer tube shaft greatly bending. In this case, the inner coil 30 of the multilayer coil 21 is going to increase in diameter and the outer coil 31 surrounding the outside of the inner coil 30 is going to reduce in diameter, and thus, a change in diameter of the multilayer coil 21 is small. If the power of the outer coil 31 to contract and the power of the inner coil 30 to expand are not well balanced, stress acts unevenly on the inner coil 30 or the outer coil 31, and plastic deformation may occur. For example, even if the number N1 of the first wires 33 of the inner coil 30 is the same as the number N2 of the second wires 34 of the outer coil 31, the inner coil 30 and the outer coil 31 have different coil diameters, and thus, the inner coil 30 and the outer coil 31 have different actions exerted thereon, such as when a compressive force acts on the inner coil 30, a tensile force acts on the outer coil 31. Therefore, when the number N1 of the first wires 33 of the inner coil 30 is set to be different from the number N2 of the second wires 34 of the outer coil 31, it is possible to adjust a balance between the power of the outer coil 31 to contract and the power of the inner coil 30 to expand to be appropriate.

When the number N1 of the first wires 33 of the inner coil 30 is equal to the number N2 of the second wires 34 of the outer coil 31, it is considered that the power of the inner coil 30 to expand is larger than the power of the outer coil 31 to contact, and the outer coil 31 is likely to be plastically deformed. Therefore, by setting the number N1 of the first wires 33 of the inner coil 30 to be smaller than the number N2 of the second wires 34 of the outer coil 31, it is possible to adjust the balance between the power of the outer coil 31 to contract and the power of the inner coil 30 to expand to be more appropriate. Accordingly, the drive shaft 20 is less likely to be plastically deformed even when receiving a strong torque, and can maintain a proper structure.

Meanwhile, when excessive load torque acts on the drive shaft 20, the coil center of the drive shaft 20 may be twisted in a spiral inside the outer tube shaft 50. Even in such a case, the drive shaft 20 is hardly plastically deformed and can maintain a proper structure, so that it can keep operating. In addition, when the coil center of the drive shaft 20 is twisted in a spiral inside the outer tube shaft 50, the drive shaft 20 may come into contact with the outer tube shaft 50 located outside or the guide wire lumen tube 40 located inside. Even in such a case, a change in shape of the drive shaft 20 is limited by adjusting the balance between the power of the outer coil 31 to contract and the power of the inner coil 30 to expand to be appropriate, whereby the drive shaft 20, the outer tube shaft 50, or the guide wire lumen tube 40 can be prevented from being damaged by the contact.

After the cutting and conveyance of the lesion L are completed, the operator presses the switch 101. As a result, the rotation of the drive shaft 20 is stopped, and the liquid feeding by the liquid feeder 150 is stopped. Thereafter, the operator removes the medical device 10 from the blood vessel, and the treatment is completed.

EXAMPLES

Multilayer coils 21 having different two-layer structures were prepared by changing the number N1 of the first wires 33 of the inner coil 30 with the number N2 of the second wires 34 of the outer coil 31 being set to 16. The number N1 of the first wires 33 of Example 1 was 4, the number N1 of the first wires 33 of Example 2 was 6, the number N1 of the first wires 33 of Example 3 was 8, the number N1 of the first wires 33 of Example 4 was 10, the number N1 of the first wires 33 of Example 5 was 12, the number N1 of the first wires 33 of Example 6 was 14, and the number N1 of the first wires 33 of Comparative Example 1 was 16. In all Examples and the Comparative Example, the outer diameter of the multilayer coil 21 was 1.0 mm, the inner diameter was 0.7 mm, the wire diameter of the first wire 33 was 0.075 mm, the wire diameter of the second wire 34 was 0.075 mm, the material of the first wire 33 was SUS304 WPB, and the material of the second wire 34 was SUS304 WPB.

Each of the prepared multilayer coils 21 was cut to a length of about 300 mm and put into a polyimide tube having an inner diameter of 1.35 mm. Then, torque was applied to the multilayer coil 21 until the multilayer coil 21 was plastically deformed, and a torque value when the multilayer coil 21 was plastically deformed was measured.

Each of Examples and Comparative Example has three samples. Table 1 shows the results when the multilayer coils 21 were linearly arranged and torque was applied thereto, and Table 2 shows the results when the multilayer coils 21 were bent with a curvature radius of 15 mm and torque was applied thereto.

The results of the fracture test (plastic deformation) of the linear multilayer coils 21 shown in Table 1 indicate that Examples 1 to 6 in which the ratio Ra was less than 1 provided higher torsional strength than Comparative Example 1 in which the ratio Ra was 1. Further, in Table 1, Examples 1 to 6 in which the ratio Ra was 0.875 or less provided higher torsional strength than the Comparative Example; Examples 1 to 5 in which the ratio Ra was 0.75 or less provided higher torsional strength than Example 6; and Examples 1 to 4 in which the ratio Ra was 0.625 or less provided higher torsional strength than Example 6 and Example 5.

The results of the fracture test or plastic deformation of the bent multilayer coils 21 shown in Table 2 indicate that Examples 1 to 6 in which the ratio Ra was less than 1 provided higher torsional strength than Comparative Example 1 in which the ratio Ra was 1. Further, in Table 2, Examples 1 to 6 in which the ratio Ra was 0.875 or less provided higher torsional strength than the Comparative Example; Examples 1 to 5 in which the ratio Ra was 0.75 or less provided higher torsional strength than Example 6; Examples 1 to 4 in which the ratio Ra was 0.625 or less provided higher torsional strength than Example 6 and Example 5; Examples 1 to 3 in which the ratio Ra was 0.5 or less provided higher torsional strength than Example 6, Example 5 and Example 4; Examples 1 and 2 in which the ratio Ra was 0.375 or less provided higher torsional strength than Example 6, Example 5, Example 4 and Example 3; and Example 1 in which the ratio Ra was 0.25 or less provided higher torsional strength than Example 6, Example 5, Example 4, Example 3 and Example 2.

TABLE 1

| | | Example 1 | Example 2 | Example 3 | Example 4 | Example 5 | Example 6 | Comparative Example 1 |
|---|---|---|---|---|---|---|---|---|
| Number of wires of first coil/number of wires of second coil | | 4/16 | 6/16 | 8/16 | 10/16 | 12/16 | 14/16 | 16/16 |
| Ratio Ra | | 0.25 | 0.375 | 0.5 | 0.625 | 0.75 | 0.875 | 1 |
| Measured torque | Sample No. 1 | 47.75N mm | 51.50N mm | 54.00N mm | 58.70N mm | 41.10N mm | 16.65N mm | 12.70N mm |
| | Sample No. 2 | 47.55N mm | 49.70N mm | 54.10N mm | 56.80N mm | 40.80N mm | 17.75N mm | 11.60N mm |
| | Sample No. 3 | 47.70N mm | 48.50N mm | 52.80N mm | 59.70N mm | 38.40N mm | 14.85N mm | 12.50N mm |

TABLE 2

| | | Example 1 | Example 2 | Example 3 | Example 4 | Example 5 | Example 6 | Comparative Example 1 |
|---|---|---|---|---|---|---|---|---|
| Number of wires of first coil/number of wires of second coil | | 4/16 | 6/16 | 8/16 | 10/16 | 12/16 | 14/16 | 16/16 |
| Ratio Ra | | 0.25 | 0.375 | 0.5 | 0.625 | 0.75 | 0.875 | 1 |
| Measured torque | Sample No. 1 | 20.10N mm | 18.75N mm | 18.65N mm | 16.05N mm | 13.55N mm | 8.15N mm | 4.35N mm |
| | Sample No. 2 | 22.10N mm | 19.35N mm | 19.45N mm | 16.75N mm | 11.65N mm | 6.70N mm | 6.10N mm |
| | Sample No. 3 | 22.10N mm | 20.05N mm | 20.15N mm | 18.10N mm | 12.45N mm | 7.80N mm | 5.25N mm |

65

As described above, the medical device 10 according to the present embodiment is elongated and insertable into a living body lumen, the medical device 10 including the drive shaft 20 having the distal end and the proximal end and having the designated predetermined direction of rotation D, the drive shaft 20 capable of rotating in response to a driving force from the proximal side and transmitting a rotational force in the distal direction X, wherein the drive shaft 20 includes: the inner coil 30 formed by winding a plurality of first wires 33 side-by-side in the circumferential direction of the drive shaft 20; and the outer coil 31 formed by winding a plurality of second wires 34 side-by-side in the circumferential direction of the drive shaft 20 and surrounding the inner coil 30, the first wires 33 of the inner coil 30 are wound in the predetermined direction of rotation D in the distal direction X as viewed from the proximal side, the second wires 34 of the outer coil 31 are wound in a direction opposite to the predetermined direction of rotation D in the distal direction X as viewed from the proximal side, and the number N1 of the first wires 33 constituting the inner coil 30 is smaller than the number N2 of the second wires 34 constituting the outer coil 31.

In the medical device 10 configured as described above, the number N1 of the wires of the inner coil 30 is smaller than the number N2 of the wires of the outer coil 31, and thus, during rotation of the drive shaft 20 in the predetermined direction of rotation D, a balance between the power of the outer coil 31 to contract and the power of the inner coil 30 to expand is improved, and the torsional rigidity of the drive shaft 20 can be improved. Therefore, the medical device 10 can suppress plastic deformation of the drive shaft 20 due to strong torque, and can properly maintain the structure of the drive shaft 20. In addition, since the balance between the power of the outer coil 31 to contract and the power of the inner coil 30 to expand is improved, the drive shaft 20 is less likely to be plastically deformed even when receiving torque in a bent state. Accordingly, the medical device 10 can simultaneously achieve smooth rotation and high torsional rigidity in a bent lesion that is tough for the medical device 10.

In addition, the number N1 of the wires of the inner coil 30 is preferably equal to or less than 0.75 times the number N2 of the wires of the outer coil 31. With this configuration, in the medical device 10, the balance between the power of the outer coil 31 to contract and the power of the inner coil 30 to expand is improved, and the torsional rigidity of the drive shaft 20 is improved. Therefore, the medical device 10 can suppress plastic deformation of the drive shaft 20 due to strong torque, and can properly maintain the structure of the drive shaft 20. Further, the medical device 10 can simultaneously achieve smooth rotation and high torsional rigidity in a bent lesion that is tough for the medical device 10.

In addition, the drive shaft 20 includes the conveyance coil 32 formed by spirally winding at least one third wire 35 at intervals in the longitudinal direction of the drive shaft 20, the conveyance coil 32 forming the outermost layer or the innermost layer of the drive shaft 20. With this configuration, when rotating, the drive shaft 20 applies a force toward the proximal side or a force toward the distal side to an object or liquid to convey the object or liquid by the conveyance coil 32 functioning as an Archimedean screw (screw pump). The conveyance coil 32 may not be provided.

In addition, the medical device 10 has an elongated inner member (for example, the guide wire lumen tube 40) disposed inside the drive shaft 20. The drive shaft 20 of the medical device 10 is easy to maintain the structure, and thus, even if the guide wire lumen tube 40 is disposed inside the drive shaft 20, it is possible to prevent the drive shaft 20 or the guide wire lumen tube 40 from being damaged due to contact between the drive shaft 20 and the guide wire lumen tube 40. Even if the coil center is twisted in a spiral due to a load torque applied to the drive shaft 20 during rotation in the predetermined direction of rotation D, the drive shaft 20 can easily maintain the structure. Therefore, it is possible to effectively prevent the drive shaft 20 or the guide wire lumen tube 40 from being damaged due to contact between the drive shaft 20 and the guide wire lumen tube 40. The inner member is not limited to a hollow member such as the guide wire lumen tube 40, and may be, for example, a solid core material.

In addition, the medical device 10 includes the cutting portion 90 directly or indirectly connected to the distal end part of the drive shaft 20 and capable of cutting an object. During cutting by the cutting portion 90, the drive shaft 20 receives a strong torque. However, the medical device 10 can suppress plastic deformation of the drive shaft 20 even if receiving a strong torque as described above. Therefore, the medical device 10 can properly maintain the structure of the drive shaft 20 even if the medical device 10 includes the cutting portion 90. Note that the cutting portion 90 may be directly connected to the distal end part of the drive shaft 20. In addition, the medical device 10 may not include the cutting portion 90 as long as it includes the drive shaft 20 to which torque is applied. For example, the drive shaft 20 may be provided not for cutting but for obtaining a conveying force by the conveyance coil 32.

The present invention is not limited to the above embodiment, and various modifications may be made by those skilled in the art. For example, the living body lumen into which the medical device 10 is inserted is not limited to a blood vessel, and may be, for example, a vascular channel, a ureter, a bile duct, a fallopian tube, a hepatic duct, or the like. Other changes, modifications and equivalents can be effected by one skilled in the art without departing from the spirit and scope of the invention as defined in the accompanying claims. It is expressly intended that all such changes, modifications and equivalents that fall within the scope of the claims are embraced by the claims.

REFERENCE SIGNS LIST

10 medical device
20 drive shaft
21 multilayer coil
30 inner coil
31 outer coil
32 conveyance coil
33 first wire
34 second wire
35 third wire
40 guide wire lumen tube (inner member)
90 cutting portion
N1 number of wires of inner coil
N2 number of wires of outer coil
Ra ratio
X distal direction

What is claimed is:

1. A medical device to cut an object in a living body lumen, the medical device comprising:

a rotatable elongated drive shaft that is rotatable in a first direction of rotation in response to a driving force applied to the elongated drive shaft;

a cutting portion operatively connected to the elongated drive shaft so that rotation of the elongated drive shaft in the first direction of rotation results in rotation of the cutting portion, the cutting portion having an outer surface configured to cut the object in the living body lumen when the cutting portion is rotated while the cutting portion is positioned in the living body lumen;

the drive shaft comprising an outer coil and an inner coil, the outer coil surrounding the inner coil so that the outer coil covers an outer surface of the inner coil;

the inner coil being comprised of a total number N1 of wires that extend helically in side-by-side relation to one another, the total number N1 of wires extending helically in the first direction of rotation in the distal direction as viewed from the proximal side, the total number N1 being a number greater than one;

the outer coil being comprised of a total number N2 of wires that extend helically in side-by-side relation to one another, the total number N2 of wires extending helically in a direction opposite the first direction of rotation in the distal direction as viewed from the proximal side, the total number N2 being a number greater than one;

a ratio of N1/N2 is less than 1;

a conveyance coil extending helically around an outer surface of the elongated drive shaft, the conveyance coil comprising axially adjacent helical windings that are axially spaced apart from one another;

an outer tubular shaft in which is positioned the elongated drive shaft, the outer tubular shaft including an inner layer and an outer layer positioned so that an inner peripheral surface of the outer layer faces an outer peripheral surface of the inner layer, the inner layer and the outer layer being spaced apart from one another so that a first lumen exists between the inner peripheral surface of the outer layer and the outer peripheral surface of the inner layer, the first lumen being fluidly connectable to a liquid feeding source so that during operation of the medical device liquid from the liquid feeding source is fed to the first lumen; and the outer layer including at least one through hole passing through the outer layer and fluidly communicating with the first lumen so that during operation of the medical device while the cutting portion is positioned in the living body lumen and liquid is being fed from the liquid feeding source to the first lumen, at least some of the liquid in the first lumen passes through the at least one through hole in the outer layer and enters the living body lumen.

2. The medical device according to claim 1, wherein the outer tubular shaft also includes a distal end portion having a proximal end portion that is connected to a distal end portion of the inner layer and a distal end portion of the outer layer.

3. The medical device according to claim 1, wherein the elongated drive shaft has a distal end fixed to a proximal end of a rotation shaft, the rotation shaft having a distal portion fixed to the cutting portion so that rotation of the elongated drive shaft results in rotation of the rotation shaft and the cutting portion.

4. The medical device according to claim 3, wherein the outer tubular shaft extends distally beyond the distal end of the elongated drive shaft.

5. The medical device according to claim 4, further comprising a bearing disposed fixed to a distal portion of the outer tubular shaft, the bearing rotatably supporting the rotation shaft.

6. The medical device according to claim 1, further comprising a guide wire tube positioned inside the elongated drive shaft, the guide wire tube having a lumen that extends throughout the guide wire tube to receive a guide wire during use of the medical device.

7. The medical device according to claim 6, wherein the guide wire tube extends distally beyond the distal end of the elongated drive shaft.

8. The medical device according to claim 6, wherein the outer tubular shaft has a distal end that extends distally beyond the distal end of the elongated drive shaft, the guide wire tube extending distally beyond both the distal end of the elongated drive shaft and the distal end of the outer tubular shaft.

9. The medical device according to claim 6, further comprising a handle operable by an operator during use of the device, the handle including a casing in which is located a proximal end tube provided with a lumen that communicates with the lumen in the guide wire tube and opens to outside the casing so that a guide wire is insertable into the lumen in the proximal end tube from outside the casing and is advanceable into the lumen in the guide wire tube.

10. The medical device according to claim 1, wherein the ratio N1/N2 is 0.875 or less.

11. The medical device according to claim 1, wherein the ratio N1/N2 is 0.750 or less.

12. An elongated medical device that is insertable into a living body lumen, the medical device comprising:

a drive shaft having a distal end and a proximal end, and being rotatable in a predetermined direction of rotation in response to a driving force from a proximal side of the drive shaft to transmit a rotational force in a distal direction;

a cutting portion configured to cut an object in the living body lumen when the cutting portion is rotated while the cutting portion is positioned in the living body lumen to produce cut objects, the cutting portion being operatively connected to the drive shaft so that rotation of the drive shaft causes rotation of the cutting portion, the cutting portion having a most distal end and a most proximal end;

the drive shaft comprising:

an inner coil comprised of a plurality of wires wound side-by-side in a circumferential direction of the drive shaft;

an outer coil comprised of a plurality of wires wound side-by-side in the circumferential direction of the drive shaft, the outer coil surrounding the inner coil;

the plurality of wires of the inner coil being wound in the predetermined direction of rotation toward the distal direction as viewed from the proximal side;

the plurality of wires of the outer coil being wound in a direction opposite to the predetermined direction of rotation in the distal direction as viewed from the proximal side; a total number of the plurality of wires constituting the inner coil being smaller than a total number of the plurality of wires constituting the outer coil;

the drive shaft including a conveyance coil comprised of at least one wire spirally wound in a longitudinal direction of the drive shaft, the conveyance coil forming an outermost layer or an innermost layer of the drive shaft;

a guide wire lumen tube disposed inside the drive shaft, the guide wire lumen tube extending from a most distal end of the guide wire lumen tube to a most proximal end of the guide wire lumen tube, the most distal end of the guide wire lumen tube being an open end and the most proximal end of the guide wire lumen tube being an open end, the guide wire lumen tube having a guide wire lumen configured to receive a guide wire, the guide wire lumen extending from the most distal end of the guide wire lumen tube to the most proximal end of the guide wire lumen tube;

the guide wire lumen tube having an outer surface and the inner coil having an inner surface;

a space between the outer surface of the guide wire lumen tube and the inner surface of the inner coil;

the most distal end of the guide wire lumen tube being positioned on a distal side of the distal end of the drive shaft; and the most distal end of the guide wire lumen tube being positioned between the most distal end of the cutting portion and the most proximal end of the cutting portion.

13. The medical device according to claim 12, wherein the total number of the wires of the inner coil is equal to or less than 0.75 times the total number of the wires of the outer coil.

14. The medical device according to claim 12, further comprising an elongated inner member disposed inside the drive shaft.

15. The medical device according to claim 12, further comprising a distal end opening located on the proximal side of the cutting portion, the distal end opening being in fluid communication with a second lumen and fluidly communicating the second lumen with an exterior of the cutting portion so that during operation of the medical device while the cutting portion is positioned in the living body lumen, the cut objects and blood in the living body lumen enter the second lumen by way of the distal end opening and are conveyed toward the waste holder by the conveyance coil.

16. The medical device according to claim 12, further comprising:

an outer tubular shaft in which is positioned the elongated drive shaft, the outer tubular shaft including an inner layer and an outer layer positioned so that an inner peripheral surface of the outer layer faces an outer peripheral surface of the inner layer, the inner layer and the outer layer being spaced apart from one another so that a first lumen exists between the inner peripheral surface of the outer layer and the outer peripheral surface of the inner layer, the first lumen being fluidly connectable to a liquid feeding source so that during operation of the medical device liquid from the liquid feeding source is fed to the first lumen;

the inner layer having an inner peripheral surface that faces an outer peripheral surface of the drive shaft and that is spaced from the outer peripheral surface of the drive shaft so that a second lumen exists between the inner peripheral surface of the inner layer and the outer peripheral surface of the drive shaft, the second lumen being fluidly connectable to a waste holder so that during operation of the medical device while the cutting portion is positioned in the living body lumen, the cut objects are fed along the second lumen toward the waste holder; and the inner layer including at least one through hole passing through the inner layer to fluidly communicate the first lumen and the second lumen so that during operation of the medical device while the cutting portion is positioned in the living body lumen and liquid is being fed from the liquid feeding source to the first lumen, at least some of the liquid in the first lumen enters the second lumen by way of the at least one through hole in the inner layer and flows with the cut objects toward the waste holder.

17. The medical device according to claim 12, further comprising:

a handle configured to be held by an operator to during use of the medical device, the handle including a handle interior;

a drive unit housed in the handle interior and fixed to the proximal end of the drive shaft to apply the driving force to the drive shaft;

a proximal portion of the guide wire lumen tube being positioned in the handle interior; and the guide wire lumen being in communication with an exterior of the handle interior.

18. A medical device to cut an object in a living body lumen, the medical device comprising:

a rotatable drive shaft that is rotatable in a first direction of rotation in response to a driving force applied to the drive shaft;

a cutting portion operatively connected to the drive shaft so that rotation of the drive shaft in the first direction of rotation results in rotation of the cutting portion, the cutting portion having an outer surface configured to cut the object in the living body lumen when the cutting portion is rotated while the cutting portion is positioned in the living body lumen;

the drive shaft comprising an outer coil and an inner coil, the outer coil surrounding the inner coil so that the outer coil covers an outer surface of the inner coil;

the inner coil being comprised of a total number N1 of wires that extend helically in side-by-side relation to one another, the total number N1 of wires extending helically in the first direction of rotation in the distal direction as viewed from the proximal side, the total number N1 being a number greater than one;

the outer coil being comprised of a total number N2 of wires that extend helically in side-by-side relation to one another, the total number N2 of wires extending helically in a direction opposite the first direction of rotation in the distal direction as viewed from the proximal side, the total number N2 being a number greater than one;

N1/N2 being less than 1;

an outer tubular shaft in which is positioned the drive shaft, the outer tubular shaft including an inner layer and an outer layer positioned so that an inner peripheral surface of the outer layer faces an outer peripheral surface of the inner layer, the inner layer and the outer layer being spaced apart from one another so that a first lumen exists between the inner peripheral surface of the outer layer and the outer peripheral surface of the inner layer, the first lumen being fluidly connectable to a liquid feeding source so that during operation of the medical device liquid from the liquid feeding source is fed to the first lumen;

the outer layer including at least one through hole passing through the outer layer and fluidly communicating the first lumen with outside the medical device so that during operation of the medical device while the cutting portion is positioned in the living body lumen and liquid is being fed from the liquid feeding source to the first lumen, a first portion of the liquid in the first lumen passes through the at least one through hole in the outer layer and enters the living body lumen;

the inner layer having an inner peripheral surface that faces an outer peripheral surface of the drive shaft so that a second lumen exists between the inner peripheral surface of the inner layer and the outer peripheral surface of the drive shaft, the inner layer including at least one through hole passing through the inner layer and fluidly communicating the first and second lumens so that during operation of the medical device while the cutting portion is positioned in the living body lumen and liquid is being fed from the liquid feeding source to the first lumen, a second portion of the liquid in the first lumen passes through the at least one through hole in the inner layer and enters the second lumen; and the second lumen being in fluid communication with a distal end opening located on a distal side of the at least one through hole in the inner layer and being fluidly connectable to a waste holder that is on the proximal side of the at least one through hole in the inner layer so that during operation of the medical device while the cutting portion is positioned in the living body lumen, the cut objects, blood and at least some of the first portion of the liquid that entered the living body lumen by way of the at least one through hole in the outer layer pass through the distal end opening, enter the second lumen and are conveyed toward the waste holder together with at least some of the second portion of the liquid that entered the second lumen by way of the at least one through hole in the inner layer.

19. The medical device according to claim 18, further comprising a conveyance coil extending helically around an outer surface of the outer coil and positioned in the second lumen, the conveyance coil comprising axially adjacent helical windings that are axially spaced apart from one another.

20. The medical device according to claim 18, further comprising a distal end portion having a proximal end portion connected to the drive shaft, the distal end opening being located on the distal side of a most distal end of the outer tubular shaft.

21. The medical device according to claim 18, further comprising a guide wire tube positioned inside the drive shaft, the guide wire tube having a lumen that extends throughout the guide wire tube to receive a guide wire during use of the medical device, the guide wire tube having a most distal end positioned on the proximal side of a most distal end of the cutter portion.

* * * * *